(12) United States Patent
Pollack

(10) Patent No.: US 7,060,113 B1
(45) Date of Patent: *Jun. 13, 2006

(54) HAIR COLORING COMPOSITION AND METHOD

(75) Inventor: George Pollack, Fairlawn, NJ (US)

(73) Assignee: HairMarker LLC, Sante Fe, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/568,830

(22) Filed: May 11, 2000

(51) Int. Cl.
*A61K 7/13* (2006.01)

(52) U.S. Cl. ............... 8/407; 8/426; 8/552; 8/553; 8/569; 8/606

(58) Field of Classification Search ............ 8/405, 8/407, 426, 437, 454, 462, 552, 553, 569, 8/606
See application file for complete search history.

(56) References Cited

U.S. PATENT DOCUMENTS

| 3,617,165 | A |   | 11/1971 | Kalopissis ............... 8/426 |
| 3,933,422 | A |   | 1/1976  | Saad ...................... 8/425 |
| 4,018,556 | A |   | 4/1977  | Kalopissis et al. ........ 8/415 |
| 4,153,065 | A | * | 5/1979  | Lang ........................ 132/7 |
| 5,143,723 | A |   | 9/1992  | Calvo et al. ............. 424/63 |
| 5,242,689 | A |   | 9/1993  | Yoshihara et al. ....... 424/401 |
| 5,324,506 | A |   | 6/1994  | Calvo et al. ............. 424/63 |
| 5,454,841 | A |   | 10/1995 | Wolfram et al. ......... 8/405 |
| 5,486,629 | A |   | 1/1996  | Chan et al. ............. 552/236 |
| 5,679,114 | A |   | 10/1997 | Haning et al. ........... 8/405 |
| 5,891,200 | A |   | 4/1999  | Lim et al. ............... 8/426 |
| 5,961,664 | A |   | 10/1999 | Anderson ................ 8/405 |
| 5,964,226 | A | * | 10/1999 | Sobel ..................... 132/108 |
| 6,506,374 | B1 | * | 1/2003  | Pollack ................... 424/70.6 |

FOREIGN PATENT DOCUMENTS

| DE | 196 51 482 C1 | 4/1998 |
| WO | WO 97/44002  | 11/1997 |

\* cited by examiner

*Primary Examiner*—Eisa Elhilo
(74) *Attorney, Agent, or Firm*—Duane A. Stewart, III; Buchanan Ingersoll PC

(57) ABSTRACT

A hair coloring composition suitable for capillary flow and application by means of a wick applicator communicating to a reservoir of coloring solution. The composition contains one or more hair substantive direct dyes, a polymeric ruboff shield, and a controlled viscosity to be free flowing yet not drip or cause build-up on the hair.

14 Claims, No Drawings

US 7,060,113 B1

HAIR COLORING COMPOSITION AND METHOD

FIELD OF INVENTION

The present invention relates to a semi-permanent hair dye composition and a process for its use on hair.

BACKGROUND

Many compositions for dyeing human hair are known. These are applied directly to the hair by, for example, squeezing dye liquid through a nozzle, spraying a dye composition, or applying dye with a cotton ball or the like. Often such systems call for first applying a dye composition and then fixing it by an oxidation step using peroxide or the like.

U.S. Pat. No. 5,964,226 to Joan Lasker Sobel (which is incorporated herein by reference thereto) describes a unique hair product application system wherein hair coloring composition is maintained in a reservoir provided with an applicator tip extending from within the inside of the reservoir to absorb hair coloring solution and to deliver it to the outside of the reservoir by capillary action to an applicator tip for applying the coloring solution to the hair to be treated.

The present hair coloring composition is specifically designed to be useful in the dispensers of the type disclosed in the aforesaid hair product applicator of U.S. Pat. No. 5,964,226 and to meet its unique requirements, particularly for touching up the roots of growing hair which was previously dyed with a permanent (e.g., oxidative hair dye), for highlighting hair, and for coloring sections of hair.

BRIEF SUMMARY OF THE INVENTION

The hair dyeing composition of the present invention comprises a semipermanent dye capable of capillary flow when in solution. Such dyes typically include azo dyes, diphenyldiamine dyes or quinone-imines containing a quaternary ammonium group, anthraquinones and nitro dyes, they are generally free of foaming agents such as surfactants or detergents, have a controlled viscosity in the range of from about 0 to about 10 cps (i.e. free flowing) to be completely free-flowing and yet not drip or cause a buildup on the hair, and contain a clear polymeric dye-shield antiruboff component to prevent the transfer of the applied color from the hair to surfaces such as pillows, clothes, etc., together with a polymer of vinyl acetate and of vinyl pyrrolidone, a copolymer thereof which has been found to be particularly effective.

DETAILED DESCRIPTION

The composition of the present invention must meet various requirements to be suitable for use in a hair dye applicator with a capillary flow applicator, for coloring hair roots, highlighting and section coloring of hair. The method of the present invention involves applying the hair dye composition of the present invention through a capillary applicator to the hair, wherein the material of the capillary applicator tip ranges into a reservoir containing the hair dye composition of the present invention.

Suitably the composition has to contain a semipermanent dye capable of retention through a number of shampoos. It must flow through a capillary applicator tip without clogging. It should be capable of instantaneous application upon touching the hair; it must not drip. The dyes must be capable of penetrating the cuticle of the hair without leaving an undesirable coating. It should be non-foaming especially (when filling of the reservoir), and should be quick drying. The composition should contain a shielding antiruboff component to safeguard against color being transferred from the hair to pillows and other surfaces. It should have a sufficiently, low viscosity so that the composition flows easily from the applicator tip by capillary action. Suitable pH to allow more permanence on the hair.

A principal feature of the present invention is the use of a hair substantive semipermanent dye. Suitable dyes are generally water or alcohol soluble, and are safe for use on human hair. Many other dyes tend generally not to flow through the wick and applicator and tend to clog the system.

Particularly suitable semipermanent dyes include azo dyes, diphenylamine dyes, quinone-imines containing a quaternary ammonium group, anthraquinones and nitro dyes.

The dyes are moreover capable of being instantly deposited on the hair. They allow for repeated touching to the hair with increased coverage upon each application. They penetrate the hair shaft leaving a clean, non-messy level of color molecules on the hair. No unsightly mess is left on the hair or scalp on drying.

The composition is free of surfactants and/or detergents to be non-foaming. Level application is promoted by the use of an alcohol solvent system, e.g., ethyl alcohol, isopropyl alcohol or a butyl alcohol.

Quick drying with a safe and clean solvent was realized with an alcohol system such as with ethyl alcohol. It has a pleasant odor and works with water to evaporate at a faster rate than water alone. Isopropyl alcohol could also be used but it has a less desirable odor. Butyl alcohol, such as a tert butyl alcohol or 2-butanol is also suitable as solvents for direct dyes.

The protective ruboff shield component provides against ruboff of the color to objects coming into contact with dyed hair, e.g., pillow cases, clothing, etc. The polymeric ruboff shield should not interfere with the coloring process. The polymer used in the present composition is compatible with the hair while forming a ruboff shield that surrounds each hair shaft and is gradually removed upon each subsequent shampooing.

Polyvinylpyrrolidone alone or copolymers of vinyl acetate and vinylpyrrolidone monomers are particularly effective to serve this purpose, because they are not tacky and do not interfere with the free capillary flow of the dye liquids. Generally 50% solutions of these copolymers are sold by ISP Corp., and by BASF. Most or all nonionic or cationic polymers are likely to work, and many others can be identified by routine experimentation. Anionic polymers are not expected to work.

The viscosity of the composition to be used is important to be free-flowing and yet not drip or cause a build-up on the hair. Systems using standard thickening agents such as gums are not successful. A viscosity in the range of 0–10 cps, has been found to meet these requirements, more suitably between 5 and 10 cps to be free flowing.

It has been found that the composition for hair coloring should be at a pH from about 8 to about 8.5 for best semi-permanent coloring of the hair, however, the most suitable pH will also depend on the identity of the dye and its host substantivity, as will be readily known to the skilled hair colorist.

Some dyes, such as some nitro dyes, e.g. HC yellow #2, are not well or completely soluble in the aqueous alcoholic solvent. In that case the use of an additional solvent may be needed. For example butoxyethanol (butyl cellosolve) can be suitably substituted for some (e.g. 10%) of the water.

The following examples further illustrate the present invention and embodiments thereof. All parts and percentages are by weight unless otherwise indicated.

EXAMPLES

All parts and percentages in the examples and throughout the application are by weight.

COMPONENT GLOSSARY

PVP/VA is a copolymer of vinyl acetate and vinyl pyrrolidone monomers which act as a polymeric ruboff shield.

Crotein Hydrotriticum QM is a cationic wheat protein compound sold by Croda, Inc. which acts as a conditioning agent for the hair.

Dow Corning silicone 193 is a dimethicone copolyol compound used to give a shine to hair, and is sold by Dow Corning Inc.

Arianor Dyes are cationic dyes having the structures set forth below, sold by TRI-K Industries, Inc.

Lowacryl Dyes are also cationic dyes having the structure set forth below sold by the Jos. H. Lowenstein and Sons, Inc.

Examples of Arianor dyes and of Lowacryl dyes are:

306001 Arianor ® Sienna Brown  Primarily structure I with small
C.I. Basic Brown 17              amount structure II
C.I. Number 12251

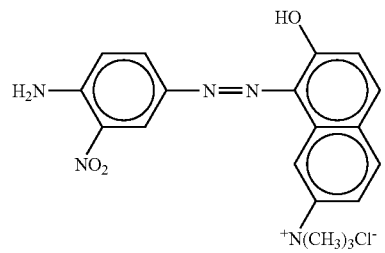

$C_{19}H_{20}N_3O_3Cl$

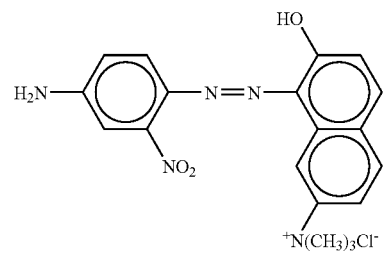

$C_{19}H_{23}N_3OCl$

306002 Arianor ® Mahogany
C.I. Basic Brown 16
C.I. Number 12550

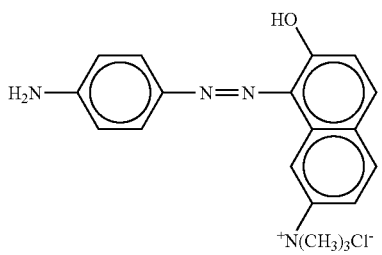

$C_{23}H_{22}N_3O_2Cl$

306003 Arianor ® Madder Red
C.I. Basic Red 76
C.I. Number 12245

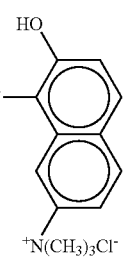

-continued
| | |
|---|---|
| 306004 Arianor ® Steel Blue<br>C.I. Basic Blue 99<br>C.I. Number 56059 | A mixture of the above structures the relative percentages of which are not precisely known<br>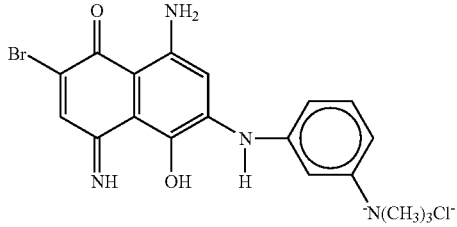<br>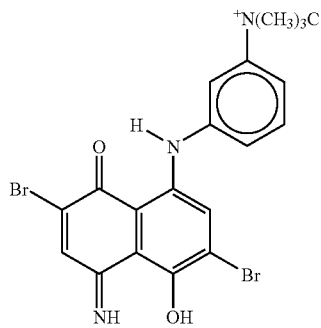 |
| 306005 Arianor ® Straw Yellow<br>C.I. Basic Yellow 57<br>C.I. Number 12719 | $C_{19}H_{22}N_3OCl$<br>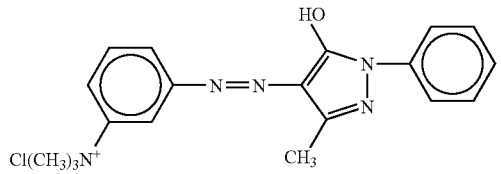 |
| Lowacryl Red 2 Conc | Lowacryl Violet 14 |
|---|---|
| | C.I Basic Violet 14 |
| CAS No: 477-73-6  MF: $C_{20}H_{19}N_4$-Cl | |
| 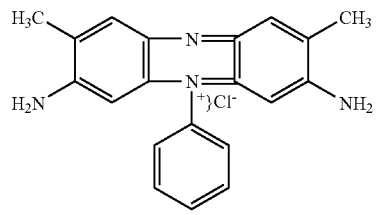 | 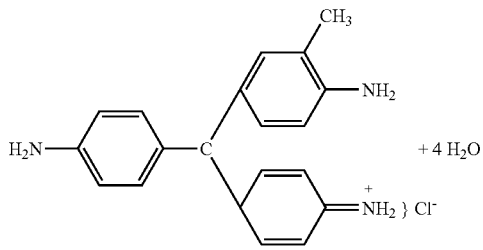 |
| EINECS No: 207-518-8  MW: 350.85 | CAS No: 632-99-5  MF: $C_{20}H_{19}N_3$-ClH·4H$_2$O<br>EINECS No: 211-189-6  MW: 409.91 |

Lowacryl Violet 4

C.I. Basic Violet 4

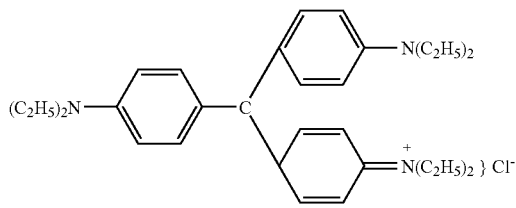

CAS No: 2390-59-2  MF: C$_{31}$H$_{42}$N$_3$-Cl

EINECS No: 219-231-5  MW: 364.92

Other names are explained in the CTFA Dictionary of Cosmetic Terms, published by the Cosmetics and Toiletries Manufacturers Association.

The hair coloring composition of the present invention will have the formula as shown below. The components are grouped in Phases A, B and C to correspond to the process steps used in their manufacture.

HAIR COLORING FORMULA

| | Percent wt |
|---|---|
| Phase A | |
| Deionized Water | 40–50 |
| PVP/VA or E735 (polymer) | 2–4 |
| Crotein Hydrotriticum QN (a cationic protein compound for conditioning) | 0.05–0.5 |
| Dow Corning silicone 193 (for shine) | 0.05–0.5 |
| Triethanolamine (ph adjuster) qs to pH 8.5 | |
| Phase B - Cationic Dyes | |
| Deionized Water | 35–40 |
| Arianor Steel Blue | 0.05–2.0 |
| Arianor Madder Red | 0.1–1.0 |
| Arianor Straw Yellow | 0.05–1.0 |
| Arianor Crazy Gold | 0.05–0.7 |
| Arianor Flame Red | 0.05–0.7 |
| Arianor Orange | 0.05–0.7 |
| Arianor Mahogany Brown | 0.050–1.0 |
| Arianor Sienna Brown | 0.05–1.0 |
| Lowacryl Violet 4 | 0.05–0.3 |
| Lowacryl Violet 14 | 0.05–0.3 |
| Lowacryl Red 2 | 0.05–0.3 |
| Phase C | |
| Ethyl Alcohol | 10–20 |
| Phase D | |
| Perfume | 0.05–0.2 |

The above formula will yield the complete range of colors needed for dyeing hair of all types of shades. If the shade is too weak it will be known to the colorist to increase the color in small increments until the desired shade is reached. If the color is too strong, a base without the color can be added until the color is the desired shade. The final pH of 8.5 is also important to dyeing the hair in a semipermanent manner.

The specific formula for a very dark brown shade is given by way of example:

| | Percent |
|---|---|
| Phase A | |
| Deionized Water | 42.0 |
| PVP/VA E 635 | 2.00 |
| Crotein hydrotriticum | 0.2 |
| Dimethicone copolyol DC 193 | 0.1 |
| Phase B | |
| Deionized Water | 33.0 |
| Arianor Steel Blue | 1.2 |
| Arianor Madder Red | 0.3 |
| Arianor Straw Yellow | 0.6 |
| Arianor Mahogany Brown | 0.2 |
| Arianor Sienna Brown | 0.2 |
| Phase C | |
| Ethanol | 20.0 |
| Phase D | |
| Triethanolamine 99% | q.s.pH = 8.0–8.5 |
| Phase E | |
| Belmay perfume Silk | 0.1 |

The composition of the present invention can be suitably prepared as follows:

Phase A

Add deionized water to a stainless steel kettle. Then add the PVP/VA copolymer and mix until clear. After the solution is clear and the polymer completely dissolved, add the Crotein Hydrotriticum QM and the dimethicone copolyol and mix until clear. Then add the triethanolamine and check the pH. Adjust to pH 8.0–8.5.

Phase B (Dyes)

In a separate stainless steel kettle add deionized water and carefully weight out the desired cationic dyes for a given shade. Mix until completely dissolved in the solution.

Then combine Phases A and B and continue mixing until uniform.

Then add Phase C containing the alcohol to the mixed Phases A and B and mix. Finally add the perfume component and mix.

Check the shade of the final composition.

Various modifications may suggest themselves to those skilled in the art with departing from the invention as defined by the following claims.

I claim:

1. A hair coloring composition for flow by capillary action, consisting essentially of a hair substantive direct cationic semipermanent dye or cationic washable color in a liquid vehicle and a polymeric ruboff protector component for preventing ruboff of the color of said direct dye, wherein said composition has a viscosity of from about 0 to about 10 cps wherein said direct cationic semipermanent dye contains a quaternary ammonium group, and wherein said composition is free of surfactants and detergents.

2. The hair coloring composition of claim 1, wherein said direct cationic semipermanent dye is one or more of an azo dye, diphenyldiamine dye, quinone-imine, an anthraquinone, and a nitro dye.

3. The hair coloring composition of claim 2, containing a plurality of said dyes, each at a concentration of from about 0.05% wt. to about 2% wt.

4. The hair coloring composition of claim 1 wherein said polymeric ruboff protector component is at least one of vinyl acetate and vinylpyrrolidone.

5. The hair coloring composition of claim 1, wherein said polymeric ruboff protector component is a copolymer of vinyl pyrrolidone and vinyl acetate.

6. The hair coloring composition of claim 1, wherein the composition has a viscosity of from about 5 to about 10 cps.

7. The hair coloring composition of claim 1, wherein said liquid vehicle comprises an alcohol solvent.

8. The hair coloring composition of claim 7, wherein said alcohol is at least one of ethyl alcohol, isopropyl alcohol, and butyl alcohol.

9. The hair coloring composition of claim 8, wherein said butyl alcohol is at least one of tert butyl alcohol, or 2-butanol.

10. A hair coloring composition capable of capillary flow from a reservoir to the tip of a fibrous applicator, consisting essentially of a cationic dye containing a quaternary ammonium group capable of directly applying color to hair without oxidation, said dye being at least one of an azo dye, diphenyldiamine dye, quinone-imine and direct nitro dyes, a liquid vehicle, and a polymeric shielding component being a copolymer of vinyl acetate and vinylpyrrolidone.

11. The composition of claim 10 having a pH of from about 8 to about 8.5.

12. A hair coloring composition capable of flow by capillary action through a fibrous applicator immersed in a reservoir containing said composition to a tip of said applicator for application to hair, consisting essentially of from about 0.05 to about 6.5 weight percent of one or more cationic direct dye containing quaternary ammonium group capable of providing color to the hair without oxidative treatment, a liquid vehicle, and from about 2 to about 4 weight percent of a polymeric shielding component to prevent the color of said composition rubbing off after application of said composition.

13. The hair coloring composition of claim 8 wherein said polymeric shielding component is a copolymer of vinylacetate and vinylpyrrolidone.

14. A method for applying the hair dye composition of claim 1 to hair, which comprises contacting a capillary applicator tip to the part of the hair to be colored thereby, with the material of said capillary applicator tip ranging into a reservoir containing said hair dye composition.

* * * * *